(12) United States Patent
Berry

(10) Patent No.: US 6,363,271 B1
(45) Date of Patent: Mar. 26, 2002

(54) AMNIOTIC FLUID ALERTING DEVICE

(76) Inventor: Daniel K. Berry, 135 Vinsant St., Brooks AFB, TX (US) 78235-1015

( * ) Notice: Subject to any disclaimer, the term of this patent is extended or adjusted under 35 U.S.C. 154(b) by 14 days.

(21) Appl. No.: 09/702,616

(22) Filed: Nov. 1, 2000

(51) Int. Cl.[7] .............................................. A61B 5/05
(52) U.S. Cl. ........................ 600/361; 600/345; 600/304
(58) Field of Search .......................... 600/361, 304, 600/300, 345, 348

(56) References Cited

U.S. PATENT DOCUMENTS

| | | | | |
|---|---|---|---|---|
| 4,281,659 A | * | 8/1981 | Farrar et al. | 600/351 |
| 4,357,945 A | * | 11/1982 | Janko | 600/584 |
| 5,425,377 A | * | 6/1995 | Caillouette | 600/572 |
| 5,577,512 A | * | 11/1996 | Caillouette | 600/572 |
| 5,664,579 A | * | 9/1997 | Caillouette | 600/572 |
| 5,738,634 A | * | 4/1998 | Caillouette | 600/572 |
| 5,928,165 A | * | 7/1999 | Caillouette | 600/572 |
| 6,126,597 A | * | 10/2000 | Smith et al. | 600/362 |
| 6,149,590 A | * | 11/2000 | Smith et al. | 600/367 |
| 6,206,840 B1 | * | 3/2001 | Abraham-Fuchs et al. | 600/584 |

* cited by examiner

*Primary Examiner*—Kevin Shaver
*Assistant Examiner*—Navin Natnithithadha
(74) *Attorney, Agent, or Firm*—Peter A. Borsari

(57) ABSTRACT

A device for implantation on the cervix of a pregnant female that provides a means by which a female patient or her health caregiver is notified of the rupture of membranes by the release of amniotic fluid. The device comprises a housing manufactured from biocompatible material having a hole through which amniotic fluid in the patient's vagina may pass. The housing contains a pH meter and a transmitter in electronic communication therewith as well as a power source for the sensor and transmitter. When amniotic fluid is released through the cervix into the vagina, a quantity thereof may pass into the housing and sensed by the sensor, causing the sensor to direct a signal to the transmitter. The transmitter issues an electronic signal to a second electronic device such as a pager or PDA, notifying the patient or her health caregiver that her water has broken.

16 Claims, 2 Drawing Sheets

AMNIOTIC FLUID ALERTING DEVICE

FIELD OF INVENTION

The present invention relates to the determination of when the amniotic fluid of a pregnant female mammal has been discharged through the cervix. More particularly, the present invention relates to a device having a pH sensor which may be implanted in the female's cervix which is capable of sensing a shift in pH of the vagina from a normally acidic condition to a basic condition caused by the influx of amniotic fluid. The device then transmits a warning signal to an auxiliary electronic device.

BACKGROUND OF THE INVENTION

It is often difficult for a pregnant woman to know when labor has begun. For example, during the last trimester of pregnancy, false labor comprising irregular and shallow contractions of the uterus, the so-called "Braxton Hicks contractions", may be confused with actual labor. Unlike true labor, these contractions are highly irregular and may be felt in the abdomen at onset rather than in the back. Furthermore, Braxton Hicks contractions are weak and do not strengthen. Despite these distinguishing characteristics, many women, especially those lacking competent care, may not be able to tell the difference between false labor and actual labor.

During the latent phase of labor (pre labor), the cervix begins thinning out and may dilate very gradually. The first stage of labor is generally considered to begin when the cervix starts to open and ends when it is fully open. Women are admitted to the hospital when the dilation of the cervix reaches about 4 cm. The vagina may be examined to determine if the membranes surrounding the fetus have ruptured and to measure how dilated and effaced the cervix is. To save the woman's energy and to avoid tearing her cervix, pushing is discouraged during the first stage of labor which may last anywhere from a few hours to 12 hours. Pushing efforts are needed during the second stage of labor which begins when the cervix has achieved a maximum dilation of about 10 cm.

In some instances, rupture of the fluid-filled membranes surrounding the fetus may occur before labor begins (the water breaks), causing leakage of the amniotic fluid through the cervix and vagina and requiring immediate medical attention. In most of these cases, labor spontaneously begins within 24 hours from the time the water breaks. In cases where labor fails to begin, labor is induced to prevent infections caused by bacteria entering the uterus from the vagina. Because the release of the amniotic fluid does not always occur as a sudden gush and may be a slow trickle resembling urinary leakage, a woman may not always be sure that her water has broken and she may fail to seek medical attention promptly. This delay may cause stress to the fetus and may endanger the health of mother and child.

"Silent labor" is a situation in which labor onset occurs without pronounced contractions. This condition occurs commonly in premature birth situations where dilatation and effacement of the cervix are not accompanied with contractions. In some cases, contractions may not begin until minutes before actual delivery.

Determining the onset of labor in non-human females may be even more unpredictable due to the inability of the animal to discuss its condition with its human caregivers. As with human labor, complications are possible which endanger both mother and children.

Once dilatation has begun, it may not proceed in a linear fashion, requiring medical personnel to repeatedly measure the amount of dilation which has occurred. In standard procedures, this involves the insertion of fingers or instruments into a woman's vagina to take measurements, taxing the time of busy personnel and the patience of the patient who is in an already uncomfortable state.

Numerous attempts have been made to provide means by which onset and conditions of labor may be evaluated and/or monitored. For example, U.S. Pat. No. 5,063,930 to Nucci shows a disposable probe comprising an elongated conduit member made of transparent plastic and having a closed end portion, an external surface and an internal surface defining an enclosed space. An oval hole is provided in the conduit member near the closed end portion and permits the collection of biological fluids. An indicator allows for the determination of the pH of the fluids collected from the vagina.

U.S. Pat. No. 5,807,281 to Welch shows an apparatus for detecting dilation of a cervix by measuring the force exerted by a cervix as it dilates at the onset of labor. The device comprises a ring-shaped element in series with an enclosure that encircles the cervix and is secured thereto by a friction tab. The enclosure contains a detectable fluid or particulate material which is released by the device to signal that the dilation has occurred.

U.S. Pat. No. 5,406,961 to Artal relates to a premature labor monitor system including a pessary having sensing means for determining the dilation and effacement of the cervix of a patient. Sensing means are provided which determine changes in the energy levels transmitted through the cervical tissue as the tissue thins and loses vascularization during the labor process. Signals are transmitted from the pessary to a patient monitor by such means as small data wires or microwave transmission generated by a small transmitter on the pessary.

U.S. Pat. No. 3,768,459 to Cannon et al. discloses a cervical dilation measuring device comprising a signal transmitting device that may be attached to one side of the cervix and a miniature receiving device attached to or placed against the opposite side of the cervix. The intensity of the signal passed from the transmitting device to the receiving device will vary as a function of the distance of separation of the devices indicating the current dilation of the cervix. Similarly, U.S. Pat. No. 5,438,996 to Kemper et al.; U.S. Pat. No. 5,851,188 to Bullard et al. and U.S. Pat. No. 5,713,371 to Sherman et al. disclose devices having transducers which are positioned on the cervix and which utilize ultrasound to determine the dilation of the cervix.

U.S. Pat. No. 4,476,871 to Hon teaches a device for monitoring cervical dilatation during labor comprising an elongated member adapted for positioning between a fetal presenting part and the cervix. Means are provided for measuring the recession of the cervix with cervical dilatation from the elongated member and along the longitudinal axis thereof.

U.S. Pat. No. 5,876,357 to Tomer relates to a labor monitoring system using a probe in the form of a linear caliper-clamp apparatus and a flexible membrane which are manually inserted into the vagina and clamped on the cervix wall. The arms of the caliper straddle the thickness of the cervical wall and the flexible membrane approximates the radius of curvature of the opening of the cervix. Sensors are used to relate this data to a monitoring unit and data processing apparatus such as a computer.

U.S. Pat. Nos. 4,719,925 and 4,682,609 both to Parsons and U.S. Pat. No. 4,207,902 Krementsov each relate to hand-actuated measuring apparatuses having a scissors-like action which may be inserted into the vagina to determine the dilatation of the cervix.

U.S. Pat. No. 3,583,389 to Harvey; U.S. Pat. No. 4,203,450 to Kegel; U.S. Pat. No. 4,055,839 to Skeggs; U.S. Pat. No. 4,264,900 to Charlier; U.S. Pat. No. 4,232,686 to Kammlade, Jr.; U.S. Pat. No. 5,776,073 to Garfield et al.; U.S. Pat. No. 5,450,837 to Garfield et al.; U.S. Pat. No. 5,879,293 to Hojaiban et al. each teach apparatuses which monitor cervical and/or other labor conditions but which are non-invasive, deriving their output from sensors applied on or about the body surface of a female patient.

Despite the teachings of the prior art, a need still exists for a device providing means to determine the expulsion of amniotic fluid from the cervix. Such a device should be securable rapidly and easily to the female body. In addition, such a device should not be obtrusively large or unduly delicate in use such that it does not pose a burden to the female patient/subject or suffer damage under normal conditions of use. Moreover, such a device should notify a patient or her health caregiver when her water breaks.

SUMMARY OF THE INVENTION

Accordingly, it is an object of the present invention to provide a device which can sense a condition of the cervix of a pregnant female and to convey information regarding the sensed condition to a health caregiver or to the patient herself at the onset of labor.

It is another object of the present invention to provide a device which is manufactured from bio-compatible materials and may be passed safely and quickly into a pregnant female's vagina and affixed her cervix.

It is an additional object of the present invention to provide a device which is neither obtrusively large nor unduly delicate in use such that it does not pose a burden to the female patient/subject or suffer damage under normal conditions of use.

It is a further object of the present invention to provide a device which may be used with pregnant female subjects who may be human or non-human.

These and other objects of the present invention are accomplished by providing an amniotic fluid alerting device comprising a hollow housing having pH sensor means therein which detect the presence of amniotic fluid and electronically transmits the detection. More specifically, in a preferred embodiment of the invention, the amniotic fluid alerting device comprises a hollow housing having a cavity in which an electronic unit is disposed. The electronic unit comprises a pH sensor which is in electronic communication with a transmitter and further comprises a source of electric power. The housing is manufactured from a bio-compatible material and preferably is saucer-shaped. The top surface of the housing has a central hole so that a fluid communication between the exterior the housing the cavity is established. The pH sensor is situated within the cavity beneath the central hole. A plurality of sutures terminating at a first end in suture anchors are attached at a second end to the housing within the cavity through pores in the bottom surface of the housing. In use, the device is inserted into the vagina of a female subject and is secured to the tissue of her cervix by the suture anchors so that the central pore opens out into the vagina. When amniotic fluid is discharged from the uterus into the vagina (the water breaks), a portion of the fluid flows through the central hole and contacts the pH sensor. In response to the basic pH (7.0 to 7.5) of amniotic fluid, the pH sensor communicates a trigger signal to the transmitter. Thereafter and in response to the trigger signal, the transmitter emits a signal to an auxiliary electronic device such as a pager to notify the patient or her health caregiver that the patient's water has broken.

BRIEF DESCRIPTION OF THE DRAWINGS

The present invention will be better understood with reference to the appended drawing sheets, wherein.

DETAILED DESCRIPTION

Figure 1:
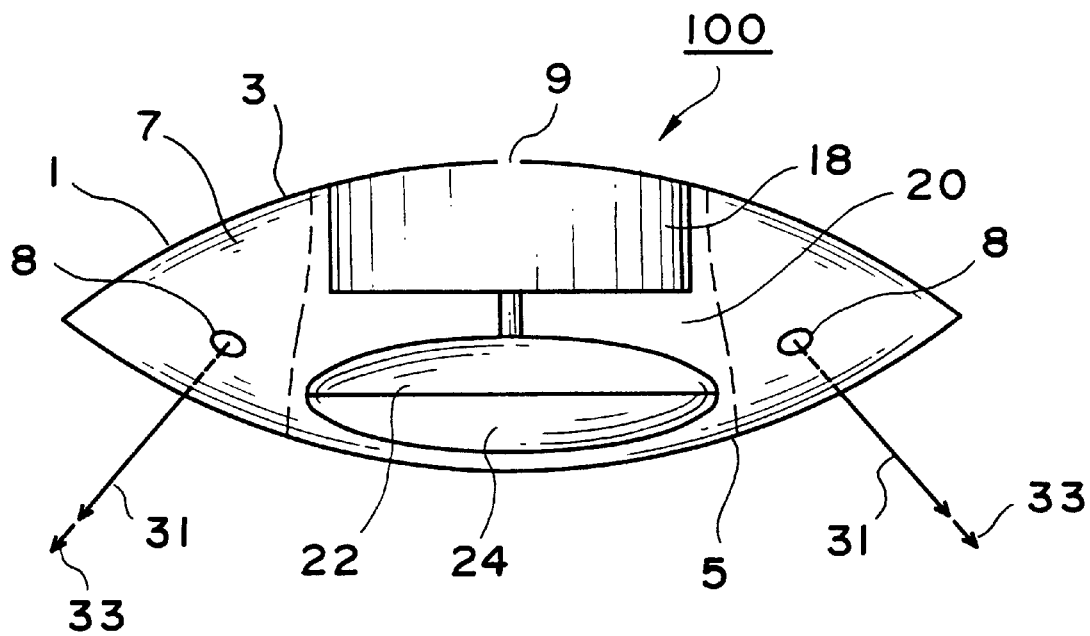
FIG. 1 is a side sectional detail view of the amniotic fluid alerting device of the present invention.
Figure 1:
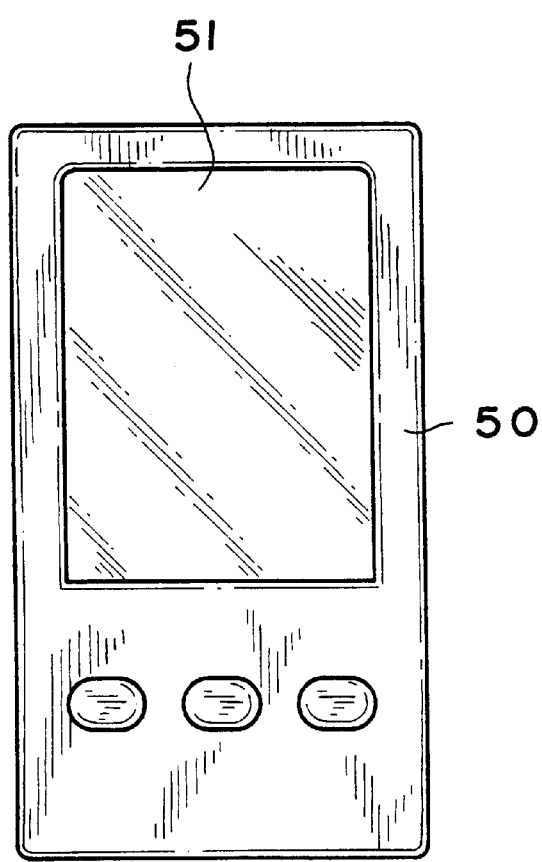
Figure 2:
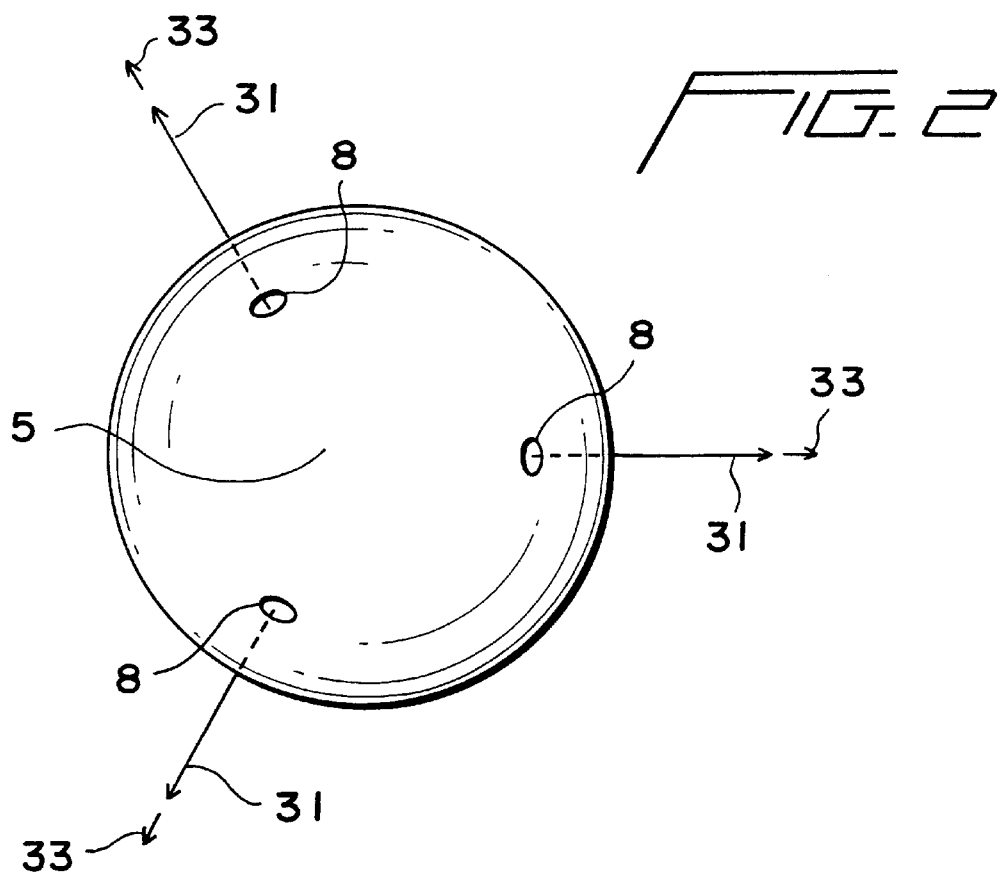
FIG. 2 is a bottom perspective view of the amniotic fluid alerting device of the instant invention.

Referring to FIGS. 1 and 2, the amniotic fluid alerting device 100 of the instant invention is seen to comprise a saucer-shaped hollow housing 1 having a top surface 3, a bottom surface 5, a cavity 7, a central hole 9 within said top surface and a plurality of pores 8 radially distributed in said bottom surface. The housing is manufactured from a bio-compatible material, suitable examples of which include polytetrafluoro-ethylene (PTFE), high-density polyethylene (HDPE) and the like. Within the cavity 7, a micro pH sensor 18 and an electronic unit 20 are housed. The pH sensor 18 is located beneath said central hole 9 and communicates with a transmitter 24 that comprises part of the electronic unit. The electronic unit further comprises a power source 22 which provides electrical energy to both the sensor and the transmitter. The pH sensor is calibrated to register a pH of 7.0 to 7.5 which is the pH of amniotic fluid. In contrast to this sensed range, normal vaginal pH is acidic and within the range of from 4.5 to 5.5.

Figure 3:
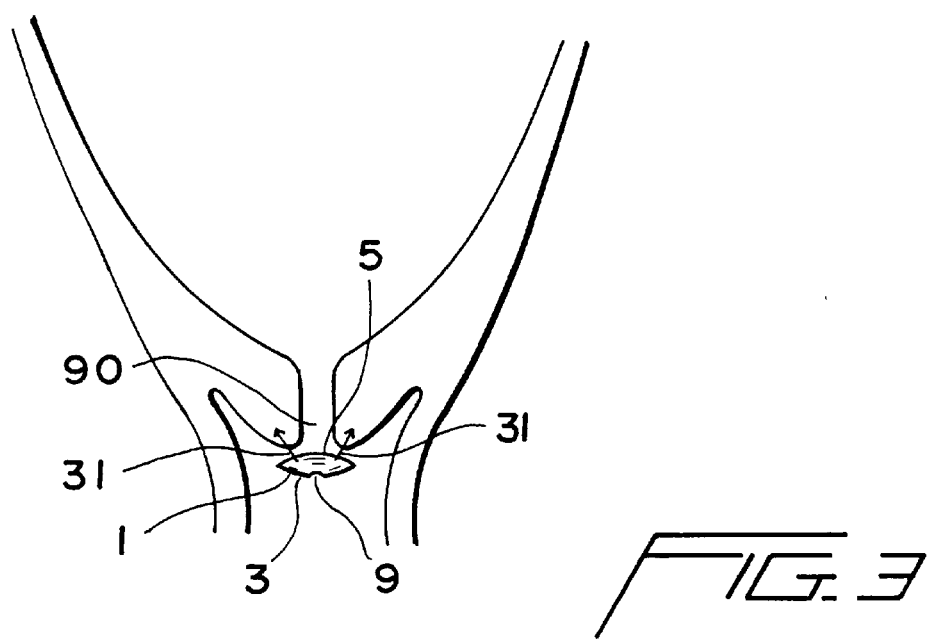
FIG. 3 is a side sectional detail view of a female uterus and cervix showing the placement of the amniotic fluid alerting device of the instant invention when affixed thereto.

As shown in FIG. 3, the amniotic fluid alerting device 100 is affixed to the cervix 90 of a female patient by at least one suture 31 which may be threaded through said plurality of pores 8. Any suitable threading arrangement can be utilized in the present invention to secure the at least one suture 31 to the cervix. In a first example of a suitable threading arrangement, the at least one suture is a plurality of sutures comprise a plurality of threads each terminating within the amniotic fluid alerting device and being fixedly attached therein. In a second example of a suitable threading arrangement, a single suture is used to secure the device to the cervix. In this second example, the suture is anchored to the cervix, passed through one of the pores into the housing, passed out of the housing by another of the pores, anchored again to the cervix, and so on in the fashion of the sewing of a button. The amniotic fluid alerting device is secured by as many suture anchors as are required to ensure that the device will not inadvertently displace from the patient's vagina. As shown in FIG. 3, the amniotic fluid alerting device is affixed in a female subject's cervix 90 in such manner that the bottom surface 5 is in contact with the cervix, whereas the top surface 3 with the central hole 9 is directed into the vagina.

When a female patient's water has broken, a quantity of amniotic fluid may enter the housing 1 through the central hole 9 to be tested by the micro pH sensor 18. A reading by the sensor of a pH within the range of 7.0 to 7.5 will trigger the sensor to communicate the presence of amniotic fluid to the transmitter 24. The transmitter 24 emits an electronic signal to a second electronic device 50 such as a pager, computer or personal digital assistant (PDA), notifying a person viewing the second electronic device 50 that the patient's water has broken. In the simplest case, the second electronic device may be a pager in the possession of the patient, the alarm of which signals the need for her to go to her health caregiver's office. Alternatively, the signal may be communicated to an electronic device in the possession of the health caregiver, so that the health caregiver may be responsible for collecting the patient and preparing the birthing center for her arrival.

The components of the labor monitoring device 100 are relatively inexpensive, thus they may be discarded after use preventing the spread of communicable diseases.

Exemplary modifications, enumerated herein, have been given to illuminate rather than to limit the scope of the invention. While particular embodiments of the invention have been described, it will be understood, of course, that the invention is not limited thereto, and that many obvious modifications and variations can be made, and that such modifications and variations are intended to fall within the scope of the appended claims.

What is claimed is:

1. An amniotic fluid alerting device comprising:
    a housing, said housing having a top surface, a bottom surface, a central cavity, a central hole disposed within said top surface and a plurality of pores radially distributed through said bottom surface;
    a pH sensor, said pH sensor being housed within said cavity and being in fluid communication with said central hole;
    an electronic transmitter in electronic communication with said pH sensor;
    an electric power source, said electric power source being in electrical communication with both said electronic transmitter and said pH sensor;
    at least one suture, said at least one suture having a first end affixed to said cavity within said housing, a second end terminating into a suture anchor, and a suture length between said first end and second end, said suture length being threaded through at least one of said plurality of pores.

2. The amniotic fluid alerting device in accordance with claim 1, wherein when said pH sensor detects a pH indicative of the presence amniotic fluid, said pH sensor communicates with said transmitter such that said transmitter emits a signal.

3. The amniotic fluid alerting device in accordance with claim 2, further comprising an auxiliary electronic device, said auxiliary electronic device being responsive to an emission from said transmitter such that said auxiliary electronic device emits a signal.

4. The amniotic fluid alerting device in accordance with claim 3, wherein said auxiliary electronic device is a paging device capable of providing a signal.

5. The amniotic fluid alerting device in accordance with claim 3, wherein said auxiliary electronic device is a personal digital assistant (PDA) capable of providing a signal.

6. The amniotic fluid alerting device in accordance with claim 3, wherein said auxiliary electronic device is a computer capable of providing a signal.

7. The amniotic fluid alerting device in accordance with claim 1, wherein said labor alerting device is manufactured from a bio-compatible material.

8. The amniotic fluid alerting device in accordance with claim 7, wherein said bio-compatible material is selected from the group consisting of polytetrafluoro-ethylene (PTFE) and high-density polyethylene (HDPE).

9. The amniotic fluid alerting device in accordance with claim 1, wherein said at least one suture is a single suture.

10. The amniotic fluid alerting device in accordance with claim 1, wherein said at least one suture is a plurality of sutures.

11. The amniotic fluid alerting device in accordance with claim 7, wherein said labor alerting device is suitable for implantation on the cervix of a female mammal.

12. The amniotic fluid alerting device in accordance with claim 9, wherein said female mammal is a human female.

13. The amniotic fluid alerting device in accordance with claim 1, wherein said pH sensor is responsive within a pH range of from 7.0 to 7.5.

14. The amniotic fluid alerting device in accordance with claim 1, wherein said housing is saucer-shaped.

15. A method for using the amniotic fluid alerting device in accordance with claim 1 comprising the steps of:
    (a) placing said amniotic fluid alerting device within vagina of a female mammal in such a manner that said top surface is directed into the vagina and said bottom surface is in contact with the cervix of a female mammal, and
    (b) affixing said suture anchor of said second end of said at least one suture to the cervix of a female mammal, thereby securing said alerting device to the cervix of a female mammal;
    wherein, when amniotic fluid within the vagina of said female mammal enters said central hole disposed within said top surface of said house, the amniotic fluid is detected by said pH sensor, thereby causing said pH sensor to electronically communicate with said transmitter in order to emit a signal.

16. The method for using the amniotic fluid alerting device in accordance with claim 15, wherein said signal is emitted to an auxiliary electronic device.

* * * * *